United States Patent
Bradley et al.

(10) Patent No.: US 9,770,326 B2
(45) Date of Patent: Sep. 26, 2017

(54) MULTIFOCAL CORRECTION PROVIDING IMPROVED QUALITY OF VISION

(71) Applicants: Arthur Bradley, Bloomington, IN (US); Peter S. Kollbaum, Bloomington, IN (US); Larry N. Thibos, Bloomington, IN (US)

(72) Inventors: Arthur Bradley, Bloomington, IN (US); Peter S. Kollbaum, Bloomington, IN (US); Larry N. Thibos, Bloomington, IN (US)

(*) Notice: Subject to any disclaimer, the term of this patent is extended or adjusted under 35 U.S.C. 154(b) by 0 days.

(21) Appl. No.: 14/514,668

(22) Filed: Oct. 15, 2014

(65) Prior Publication Data

US 2015/0029460 A1 Jan. 29, 2015

Related U.S. Application Data

(63) Continuation of application No. 13/405,395, filed on Feb. 27, 2012, now Pat. No. 8,894,203, which is a (Continued)

(51) Int. Cl.
*A61F 2/16* (2006.01)
*A61F 2/14* (2006.01)
(Continued)

(52) U.S. Cl.
CPC ............ *A61F 2/1613* (2013.01); *A61F 2/145* (2013.01); *A61F 2/1451* (2015.04);
(Continued)

(58) Field of Classification Search
CPC . G02C 7/02; G02C 7/04; G02C 7/041; G02C 7/042; G02C 7/044; G02C 7/049;
(Continued)

(56) References Cited

U.S. PATENT DOCUMENTS 5,089,024 A 2/1992 Christie et al.
5,112,351 A 5/1992 Christie et al.
(Continued)

FOREIGN PATENT DOCUMENTS

CN 1582408 A 2/2005
CN 1909860 2/2007
(Continued)

OTHER PUBLICATIONS

English Translation of Korean Office Action issued for Korean Application No. 10-2012-7008575, dated Mar. 7, 2016, 18 pages.
(Continued)

*Primary Examiner* — Jordan Schwartz
(74) *Attorney, Agent, or Firm* — Haynes and Boone, LLP

(57) ABSTRACT

This invention describes strategies and devices for improving the visual experience while expanding the depth of field of presbyopic and pseudophakic patients. The invention describes strategies and devices for providing improved image quality and improved visual quality of patients employing simultaneous vision bifocal, trifocal or multifocal corrections or monovision. The invention describes strategies and devices for reducing the visibility of the defocused part of the retinal image generated by simultaneous vision bifocal and multifocal ophthalmic corrections and monovision. The invention describes strategies and devices that employ control of spherical aberration or other similar asphericities to reduce the visibility of defocused ghost images. The invention describes strategies and devices that ensure that negative defocus is always coupled with negative spherical aberration (or similar asphericity), and that positive defocus is always coupled with positive SA (or similar asphericity) as a means to reduce the visibility of defocused ghost images.

8 Claims, 5 Drawing Sheets

Related U.S. Application Data continuation of application No. PCT/US2010/047138, filed on Aug. 30, 2010.

(60) Provisional application No. 61/238,774, filed on Sep. 1, 2009.

(51) Int. Cl.
  *G02C 7/04* (2006.01)
  *G02C 7/06* (2006.01)
  *G02C 7/02* (2006.01)

(52) U.S. Cl.
  CPC .......... *A61F 2/1616* (2013.01); *A61F 2/1618* (2013.01); *G02C 7/02* (2013.01); *G02C 7/041* (2013.01); *G02C 7/06* (2013.01)

(58) Field of Classification Search
  CPC ... G02C 7/06; A61F 2/14; A61F 2/142; A61F 2/145; A61F 2/1451; A61F 2/16; A61F 2/1602; A61F 2/1613; A61F 2/1616; A61F 2/1618; A61F 2/1621
  USPC .......................... 351/159.09, 159.11, 159.15
  See application file for complete search history.

(56) References Cited

U.S. PATENT DOCUMENTS

| | | | |
|---|---|---|---|
| 5,220,359 A | 6/1993 | Roffman | |
| 6,199,982 B1 | 3/2001 | Oyama et al. | |
| 6,457,826 B1 | 10/2002 | Lett | |
| 6,554,859 B1 | 4/2003 | Lang et al. | |
| 6,923,539 B2 | 8/2005 | Simpson et al. | |
| 7,118,214 B2 | 10/2006 | Cox | |
| 7,261,412 B2 | 8/2007 | Somani et al. | |
| 7,287,852 B2 | 10/2007 | Fiala | |
| 7,914,149 B2 | 3/2011 | Seiler | |
| 8,684,520 B2 | 4/2014 | Lindacher et al. | |
| 2004/0155312 A1 | 8/2004 | Muller-Lierheim | |
| 2006/0244906 A1* | 11/2006 | Piers .................. | A61B 3/0025 351/159.05 |
| 2009/0062911 A1 | 3/2009 | Bogaert | |
| 2009/0262301 A1* | 10/2009 | Zuba ....................... | G02C 7/04 351/159.38 |
| 2009/0268155 A1* | 10/2009 | Weeber ................ | A61F 2/1618 351/159.05 |
| 2010/0057202 A1* | 3/2010 | Bogaert ................... | G02C 7/04 623/6.27 |
| 2010/0097569 A1* | 4/2010 | Weeber ................. | A61F 2/1618 351/159.44 |
| 2010/0234943 A1 | 9/2010 | Portney | |
| 2011/0019148 A1* | 1/2011 | Portney ................. | G02C 7/041 351/159.06 |
| 2011/0029073 A1* | 2/2011 | Liang ..................... | A61F 2/147 623/5.11 |
| 2011/0310347 A1 | 12/2011 | Lindacher et al. | |

FOREIGN PATENT DOCUMENTS

| | | |
|---|---|---|
| CN | 1971341 | 5/2007 |
| JP | 2002-536685 A | 10/2002 |
| JP | 2003-531677 | 10/2003 |
| JP | 2006-517676 A | 7/2006 |
| KR | 1994-0013470 | 7/1994 |
| WO | WO 01/82839 | 11/2001 |
| WO | WO 02/21194 | 3/2002 |
| WO | WO 2004/049979 | 6/2004 |
| WO | WO 2005/019906 | 3/2005 |
| WO | WO 2007/015001 | 2/2007 |
| WO | WO 2009/025808 | 2/2009 |
| WO | WO 2009/029515 | 3/2009 |
| WO | WO 2009/058755 | 5/2009 |
| WO | WO 2009/100322 | 8/2009 |
| WO | WO 2009/123700 | 10/2009 |
| WO | WO 2010/014767 | 2/2010 |

OTHER PUBLICATIONS

English Translation of Japanese Office Action issued for Japanese Application No. 2012-527949, dated Dec. 1, 2015, 10 pages.
Barisic A. et al., Comparison of diffractive and refractive multifocal intraocular lenses in presbyopia treatment. Collegium antropologicum, 2008, vol. 32, No. 2, pp. 27-31.
Office Action issued in Singapore Patent application No. 10201405374Q dated Mar. 20, 2017, 12 pages.

* cited by examiner

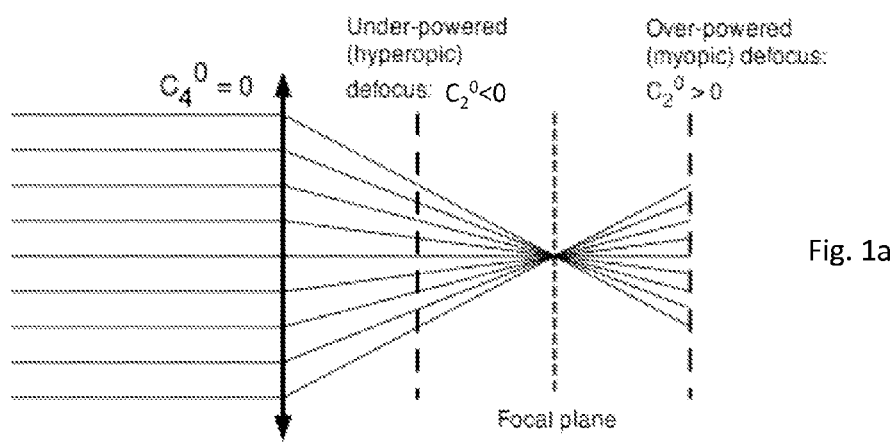
Fig. 1a
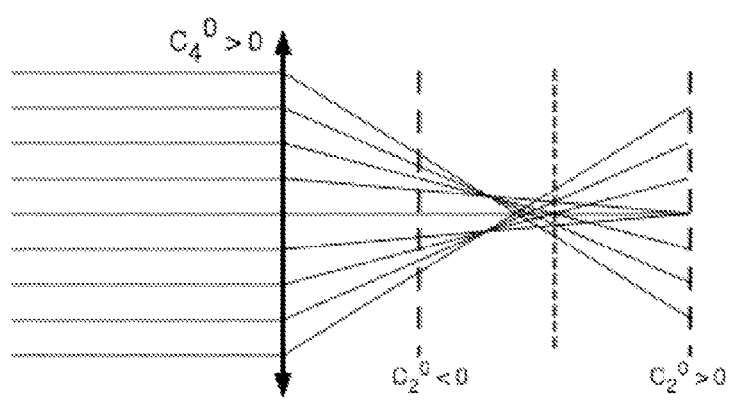
Fig. 1b
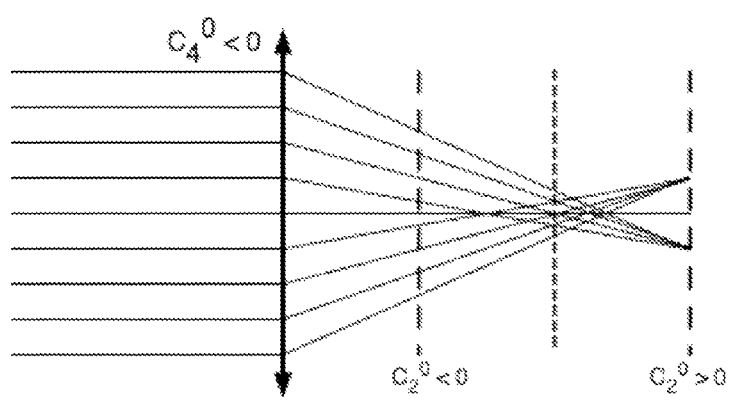
Fig. 1c
Fig. 1

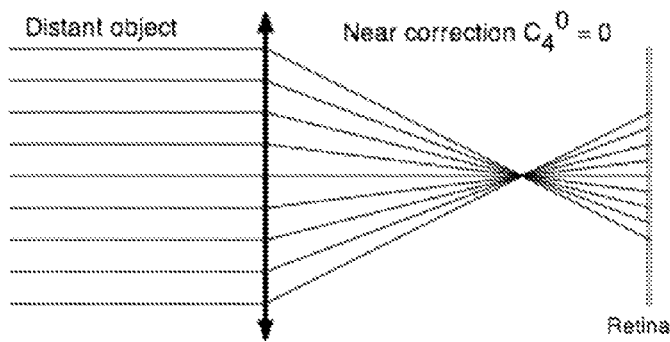
Fig. 2a
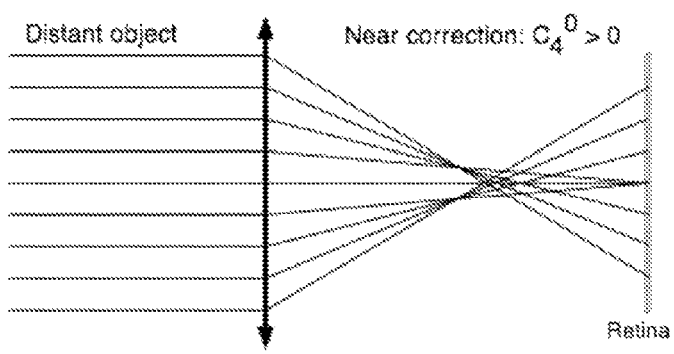
Fig. 2b
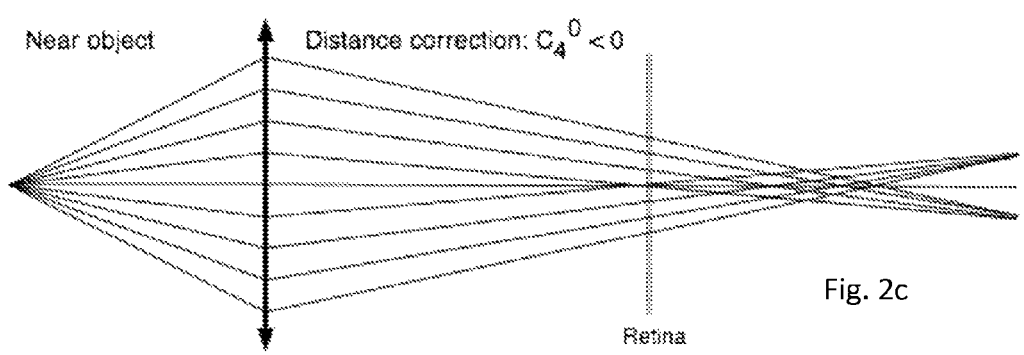
Fig. 2c
Fig. 2 ative surgery because the lenses or corneal corrections move with the eye. Therefore, irrespective of gaze direction, the patient is always looking through the same optics.

MULTIFOCAL CORRECTION PROVIDING IMPROVED QUALITY OF VISION

CROSS-REFERENCE TO RELATED APPLICATIONS

This disclosure is a continuation of and claims priority to U.S. patent application Ser. No. 13/405,395, filed on Feb. 27, 2012, which is a continuation of and claims priority to PCT Application No. PCT/US2010/047138, filed Aug. 30, 2010, which claims the benefit of U.S. Provisional Patent Application No. 61/238,774, filed on Sep. 1, 2009, each of which are incorporated by reference in their entirety.

TECHNICAL FIELD

The present invention relates generally to the field of ophthalmic optical and surgical visual corrections, and more particularly provides methods, devices, and systems for treating presbyopia and other visual conditions, and for developing prescriptions for the treatment of presbyopia and other visual conditions, and/or the like.

BACKGROUND ART

As the human eye ages, its ability to change its power to image objects at different distances wanes. This decline is called "presbyopia" and it affects all humans. A similar inability to adjust optical power of the eye's lens occurs in patients who have their natural lens replaced by an artificial lens (e.g. after cataract surgery). Thus the challenges of seeing at multiple distances faced by presbyopes are shared by pseudophakes. Currently, there is no cure for presbyopia, and there is no perfect optical treatment that will restore this full range of vision those skilled in the art and practice call "accommodation". Surrogate optical devices and strategies have been developed that are designed to increase the range of distances that can be seen (depth of field). Such devices produce what is known as "pseudo-accommodation". That is, they increase the depth of field without changing power of the eye itself. All of these devices and strategies are inferior to normal accommodation, and all require compromises by the presbyopic patient. There is an obvious need to develop improved devices and strategies to enhance the vision quality of presbyopes.

There are several well-established strategies for increasing the depth of field of presbyopes. The most simple involves implementing some form of small ("pinhole") pupil, which increases the depth of field without changing the optical characteristics of the underlying optics. Such a strategy fails in low light levels and can severely limit the size of the visual field. More typical are strategies that actively implement some optical lens or device that focuses light on the retina from targets located at different distances. One such strategy employs standard monofocal lenses of different powers in the two eyes, called "monovision". Most strategies, however, employ lenses that contain more than one power, either bifocal, trifocal, or multifocal lenses.

When implemented as a spectacle lens, the different powers present in bifocals, trifocal or multifocals are distributed across the spectacle lens, and by a combination of head and eye movements, the patient can select the region of the spectacle lens that provides a focused image on the retina (and thus high quality vision) for targets are different distances. This approach, of selecting different powers by eye and head movements will not work for soft contact lenses (CLs) or intra-ocular lenses (IOLs) or correction created in or on the cornea via refractive surgery because the lenses or corneal corrections move with the eye. Therefore, irrespective of gaze direction, the patient is always looking through the same optics.

Bifocal, Trifocal and multifocal optical corrections for presbyopes that move with the eye (corrections in or on the cornea (corneal inlays or onlays, other refractive surgeries), CLs and IOLs) must therefore contain multiple optical powers within the same or adjacent regions of the optical device or strategy that both contribute to the retinal image. That is, unlike the presbyopic spectacle lens correction in which the patient sequentially selects the physical lens location of the most appropriate optical power, patients with presbyopic corrections in CL, IOL, or refractive surgery simultaneously employ different optical powers, and thus these devices and strategies are referred to as "simultaneous vision" lenses or corrections.

Herein lies the core problem faced by CL, IOL, and refractive surgery corrections that aim to provide increased depth of field for presbyopic patients. In addition to the light that is well focused on the retina by one of the optical powers, there is simultaneously present out of focus light that is being imaged by the other power(s) in the simultaneous vision correction. The quality of the retinal image (and therefore vision of the patient) is, therefore, determined by this combination of focused and defocused light. Most of the ophthalmic industry's efforts to provide improved optical corrections for the presbyope have centered on manipulating and enhancing the focused portion of this light. The invention described in this patent is designed to improve vision of presbyopes by reducing the impact of the defocused portion of the light.

The core optical characteristic of all simultaneous vision corrections for presbyopia is the increased depth of field provided. The primary determinant of the increased depth of field is the range of optical powers within the optical device or refractive surgery. Numerous presbyopic corrections for presbyopes have been marketed and still others invented that distribute power within the lens (or refractive surgery) using a wide range of strategies. Very simply, such optical corrections can be designed to have 2 powers (bifocals), three powers (trifocals), or multiple powers (multifocals). One strategy for creating a multifocal lens is to gradually change the power of the lens from the center toward the edge. This can be achieved by introducing large amounts of spherical aberration (SA) into the lens, which can either make the lens periphery less powerful than the lens center (negative SA, see U.S. Pat. No. 7,261,412 B2, Aug. 28, 2007 and U.S. Pat. No. 0,051,876 A1, 2009). This lens would have maximum power at its center, and thus would be referred to as a "center-near" design in that increased power is required to focus near targets. Alternately, a similar strategy generates a "center-distance" design by adding positive SA to the lens (see U.S. Pat. No. 5,089,024, Feb. 18, 1992). With both of these strategies, SA is manipulated in the lens design to increase the range of powers present and thus increase the depth of field.

There is a different general strategy that employs discrete optical powers, e.g. a bifocal with two powers, or a tri-focal with three powers, rather than a gradual change in power across the lens. In such designs, the optical quality of the retinal image produced when one of the optics is in focus can be enhanced by including within each zone a complete (e.g. U.S. Pat. No. 5,220,359, Jun. 15, 1993, and World Patent # WO 2005/019906 A1) or partial (e.g. U.S. Pat. No. 7,118, 214, Oct. 10, 2006) correction for the spherical aberration (SA) present within the human eye. Because the human eye typically has positive SA, these lenses correct this by introducing negative SA. However, there may be some eyes with negative SA, so these lenses would introduce positive SA to correct it. In many such inventions, SA is first measured using some form of aberrometer.

When a controlled level of SA is introduced into a lens, this lens is often described as being "aspheric". In a third general design strategy for simultaneous vision presbyopic corrections, SA and/or other radially symmetric asphericities are employed to control the transition between zones of different powers. That is, instead of have a spatially discrete transition, the power is gradually changed across a transition region of the lens. This gradual change in power is sometimes referred to as an asphericity, or SA. Several inventions employ such asphericities (e.g. U.S. Pat. No. 6,457,826 B1, World Patent WO 2007/015001 A1, World Patent # WO 0221194 A2).

Two other strategies have been implemented that employ SA or other radially symmetric asphericities as part of a presbyopic or pseudophakic correction. First, contrary to the designs that employ a SA correction within the different optical zones to improve focused mage quality, one can introduce SA within the different zones with the goal of increasing the depth of field (e.g. U.S. Pat. No. 0,176,572 A1, 2006). Also, increased depth of field can be introduced into what is designed to be a monofocal correction by adding small asphericities to the optic (U.S. Pat. No. 0,230,299 A1, 2004).

All of the above designs that employ SA or similar asphericities are designed to either improve the quality of the focused image within a simultaneous vision correction OR to increase the depth of field in the same type of correction. One invention sought to employ SA control in a simultaneous vision lens to reduce the visibility of the defocused image (patent application WO 2010/014767). This strategy was simple: introduce specific SA into the bifocal correction that would correct for the eye's SA, and thus maximize the quality of the focused portion of the light. When the focused portion of the light was indeed well focused, this invention claimed (with no supporting evidence) that the visibility of the defocused image (often referred to as a "ghost" image) would be reduced. Of course, numerous previous patents had been awarded that already employed SA correction within the bifocal (see above). We have invented a novel strategy for employing controlled SA (or similar asphericity) to minimize the visibility of the out of focus "ghost" image generated by bifocal, trifocal or multifocal presbyopic correction (see detailed description below).

DISCLOSURE OF INVENTION

Generally described, in one aspect the present invention provides lenses, design strategies, apparatuses, methods, and systems for eliminating or minimizing the visibility of ghost images present in presbyopic corrections through the zone-specific control of the sign of spherical aberration or other asphericity. Previous art has either corrected spherical aberration or indiscriminantly induced spherical aberration without regard to the relationship between lens power and sign of SA (see above). While such approaches can be variously successful in increasing the depth of field of the presbyopic or pseudophakic eye, they produce highly visible and visually unacceptable defocused ghost images. Such ghost images reduce the overall success of these presbyopic corrections. The current art is distinct from all previous art in that either it aims to specifically couple positive SA with the most positive powered (or least negative powered) regions of the bifocal and introduce negative SA into the individual optical zone with the least positive power (or most negative power), in order to maximize depth of field while minimizing the visibility of the ghost image. Said in another way, our invention aims to introduce positive SA into the near optic and negative SA into the distant optic of a bifocal, trifocal, or multifocal CL, IOL, or refractive surgery. It requires specifically that the distance correction and near correction contain opposite sign SA to each other: negative SA in the distance correction and positive in the near correction.

BRIEF DESCRIPTION OF DRAWINGS

FIGS. 1a-c are a series of light ray diagrams depicting the focusing of light rays from a distant object by a lens with zero (a), positive (b) and negative (c) spherical aberration ($C_4^0$=0, >0 or <0, respectively). In each case the dotted vertical line represents the best focus plane (minimum RMS, circle of least confusion). The leftmost vertical dashed lines represent a plane closer to the lens which requires more focusing power than the lens has and thus generates negative defocus, or negative $C_2^0$. The rightmost vertical dashed lines represent a plane farther from the lens which requires less focusing power than the lens has and thus generates positive defocus, or positive $C_2^0$.

FIG. 2a-c are a series of light ray diagrams depicting the path of light though a lens containing no (a), positive (b), and negative (c) spherical aberration. In (b) the object is distant, while in (c) it is near. Thus in 2(b) the $C_4^0$ is positive, and, at the retinal plane, so is the defocus. In 2(c) the $C_4^0$ is negative, and at the retinal plane, so is the defocus.

MODES FOR CARRYING OUT THE INVENTION

Figure 3:
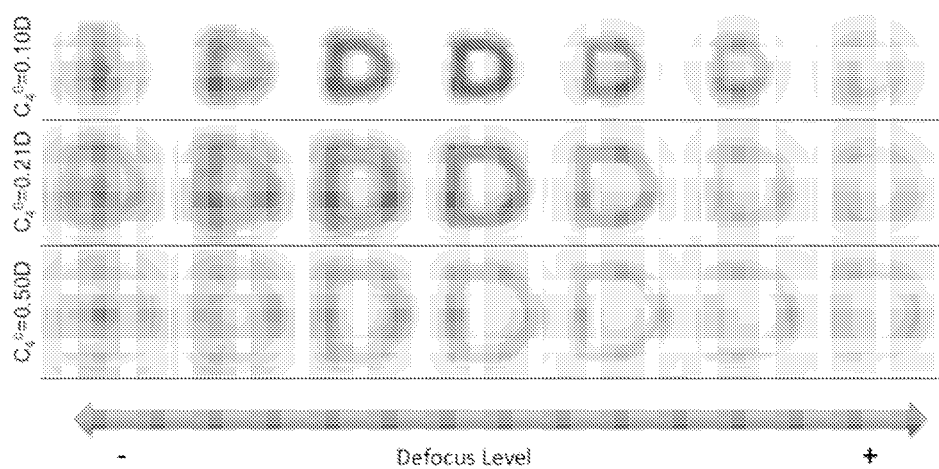
FIG. 3 illustrates the simulated retinal image of a high contrast letter D. Images are computed for a range of defocus levels, positive defocus on the right and negative defocus on the left. Three types of SA are modeled: zero SA, +0.21 Deq SA and +0.50 Deq of SA.

For the purposes of clearly, concisely and exactly describing exemplary embodiments of the invention, the manner and process of making and using the same, and to enable the practice, making and use of the same, reference will now be made to the exemplary embodiments illustrated in the figures and specific language will be used to describe the same. It will nevertheless be understood that no limitation of the scope of the invention is thereby created, and that the invention includes and protects such alterations and modifications to the illustrated embodiments, and such further applications of the embodiments illustrated and described herein as would occur to one skilled in the art to which the invention relates.

Some exemplary embodiments include lenses, design strategies, apparatuses, systems and methods for simultaneous vision contact lenses, IOLs, corneal in-lays, corneal on-lays, ophthalmic surgical prescriptions such as LASIK corrections, and other lenses or corrective prescriptions, and the like, that employ distance and near correction in combination including all forms of monovision or variants of monovision sometimes referred to a modified monovision. It shall be understood that reference to simultaneous vision lenses includes the foregoing and other corrective prescriptions. Simultaneous vision lenses include bifocal, trifocal, other multifocal lenses and the use of monofocal lenses employed in monovision prescriptions. Certain exemplary embodiments eliminate or minimize errors in these and other simultaneous vision lenses.

Exemplary embodiments include aberration control to control the visibility of the defocused portion of the image present in simultaneous vision lenses and monovision corrections. The defocused portion of the image is unavoidable in exemplary simultaneous and monovision lens strategies, and the visibility of the defocused light in the image detracts from the optical quality, and visual experience provided by such lens strategies. The visible defocused portion of the light in the image is often referred to by patients and clinicians as a ghost image or ghosting. The embodiments described herein include lenses, design strategies, apparatuses, methods, and systems for eliminating or minimizing the visibility of such ghosts. Optical principles relating to such ghosts and reduction or elimination of such ghosts will now be described in connection with FIGS. 1a, 1b, 1c, 2a, 2b, and 2c.

FIG. 1a above depicts the focusing of light rays from a distant object by a lens with positive power and zero spherical aberration (i.e. Zernike coefficient $C_4^0=0$). In FIG. 1a rays are uniformly spaced in planes of hyperopic defocus ($C_2^0<0$) and myopic defocus ($C_2^0>0$), which implies the blur circles formed in these planes are uniformly illuminated disks of light. FIG. 1b above depicts the effect of positive spherical aberration, for which the marginal rays are refracted more and the central rays are refracted less than in the upper diagram. The result is a compression of light into a pair of small high intensity blur circles in a plane of hyperopic defocus but an expansion of light into a larger, low intensity more uniform blur circle with indistinct edges in the plane of myopic defocus. FIG. 1c above depicts the effect of negative spherical aberration, for which the marginal rays are refracted less and the central rays are refracted more than in the upper diagram. The result is a compression of light into a pair of small high intensity blur circles in a plane of myopic defocus but an expansion of light into a larger, low intensity uniform blur circle in the plane of hyperopic defocus. The advantage of a larger, lower intensity uniform blur circle is a greater attenuation of contrast of the unwanted, defocused image produced by a bifocal contact lens. The disadvantage of a pair of small high intensity blur circles is diplopia or annular halo, for which disturbing ghost images or haloes of high contrast are formed on the retina.

FIGS. 2a, 2b, and 2c above illustrate the optical mechanism which is the basis for exemplary embodiments disclosed herein. Bifocal contact lenses form two retinal images of each object. One of these images will be more defocused than the other and the intention of the present invention is to reduce the conspicuousness of the image with greater defocus by reducing its contrast and overall visibility. The ray diagrams depict only the defocused portion of the image of a point source (e.g. rays for the higher powered near add optic when objects are distant, and rays from the lower powered distance optic when objects are near). FIG. 2a above depicts a defocused image of a distant object formed by that part of the bifocal implementing the near prescription for the case of zero spherical aberration. The eye is over-powered in this case, so defocus coefficient $C_2^0>0$. The blur circle on the retina is uniformly illuminated. FIG. 2b above diagram depicts the same conditions, but for a lens with positive spherical aberration ($C_4^0>0$). The result is an enlarged, lower intensity, more uniformly illuminated blur circle that de-emphasizes the blurred image by reducing its contrast. FIG. 2c above depicts imaging of light from a near target by the distance component of the prescription. Since defocus coefficient $C_2^0$ is negative in this example, the sign of spherical aberration coefficient $C_4^0$ needs to be negative to achieve the desired outcome of a large, low intensity uniformly illuminated blur circle. Note that the rationale is the same regardless of whether the center part of the bifocal contact lens provides the distance prescription and peripheral part of the lens provides the near prescription, or visa versa. Positive defocus should be coupled with positive SA, and vice versa.

Certain exemplary embodiments apply to all bifocal, multifocal and monovision corrections, can be easily understood using an example of a patient employing a bifocal simultaneous vision lens. The distance correction within such a lens focuses a distant object, but will produce defocus when viewing a near object. Conversely, the near add power of the lens will focus a near object, but will produce a defocused image when viewing a distant target. Certain exemplary embodiments disclosed herein eliminate or minimize the visibility of these defocused images (ghosts).

Patients using a bifocal lens or lenses may experience either positive or negative spherical aberration ("SA") (patients often experience positive SA, but some eyes, and some patients with high power negative lenses may have negative SA). Certain exemplary embodiments ensure that the defocused image of a near object (created the distance power of the lens), or the defocused image of a distant target (created by the add power of the lens) will co-occur with the same sign to that of the SA. Certain embodiments provide independent control of the spherical aberration in the distance and near optics to minimize undesired effects of the defocused images of both distant and near targets. Some embodiments include simultaneous vision lenses which minimize visibility of out of focus ghosts. These and other embodiments have been shown to offer improvement in the vision correction that patients experience.

Certain exemplary embodiments include bifocal or monovison type lenses or refractive surgeries that employ opposite sign SA in the distance and near optics. Specifically, the near add will include positive SA, while the distance optics will include negative SA, because the defocus caused by the near add occur due to positive defocus (excess power) when looking at distant target. Conversely, the distance correction will include negative SA because the defocus caused by the distance correction will be negative (insufficient power) when the target is near. That is unlike current art which produces lenses and optics that either have positive OR negative SA for the entire correction, or asphericities at the transitions zones, certain exemplary embodiments ensure opposite sign SA for the near and distance correction.

Some exemplary lens designs employ knowledge of patient's Spherical Aberration to create bifocal/multifocal contact lens, intraocular lens (IOL) and other lens designs in which the out of focus ghost image visibility is minimized. Image quality in an eye corrected with a simultaneous vision bifocal can be modeled by the quality of the focused image and the characteristics of the defocused image which are simultaneously present. Ocular SA can be included into the design or implementation of this opposite sign SA invention.

Some embodiments improve simultaneous vision by improving the defocused image as a function of levels and types of HOAs. In FIG. 3 it can be seen that eyes with positive SA, the retinal image of an eye with positive defocus (excess of power) is very different from the image generated with negative defocus (insufficient power). The former has low contrast and blurred edges, and thus poor visibility, whereas the latter can have high contrast and can be spatially distorted due to phase changes in the image. An exemplary design goal for a simultaneous vision bifocal is to make the defocused image have low visibility. Thus, for an eye with typical levels of positive SA, the new lens design would ensure that the near optical zone (the one defocused because of an excess in power when viewing distance targets) would have positive SA when on the eye. Also, when the distance portion of the lens is defocused (due to insufficient power when viewing a near target) it will have negative SA when on the eye. The level of SA in the eye+lens combination is the sum of that contributed by the eye and by the lens.

Using computational optics tools the inventors have generated simulated retinal images of eyes with exemplary bifocal optics. A comparison of the two examples shown in FIG. 4 and FIG. 5 shows the difference in bifocal image quality when the sign of the defocus and SA are the same (FIG. 4) and when they are opposite (FIG. 5).

Figure 4:
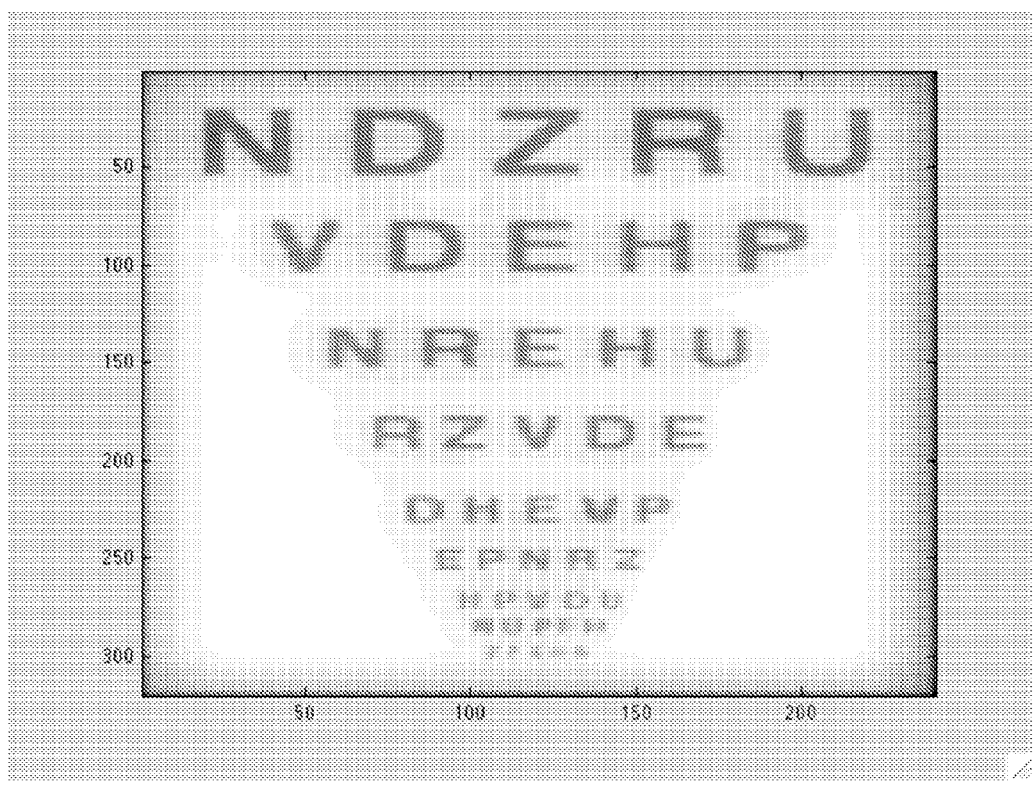
FIG. 4 illustrates the simulated retinal image of a bifocal-corrected eye generated with same sign defocus and spherical aberration.
Figure 5:
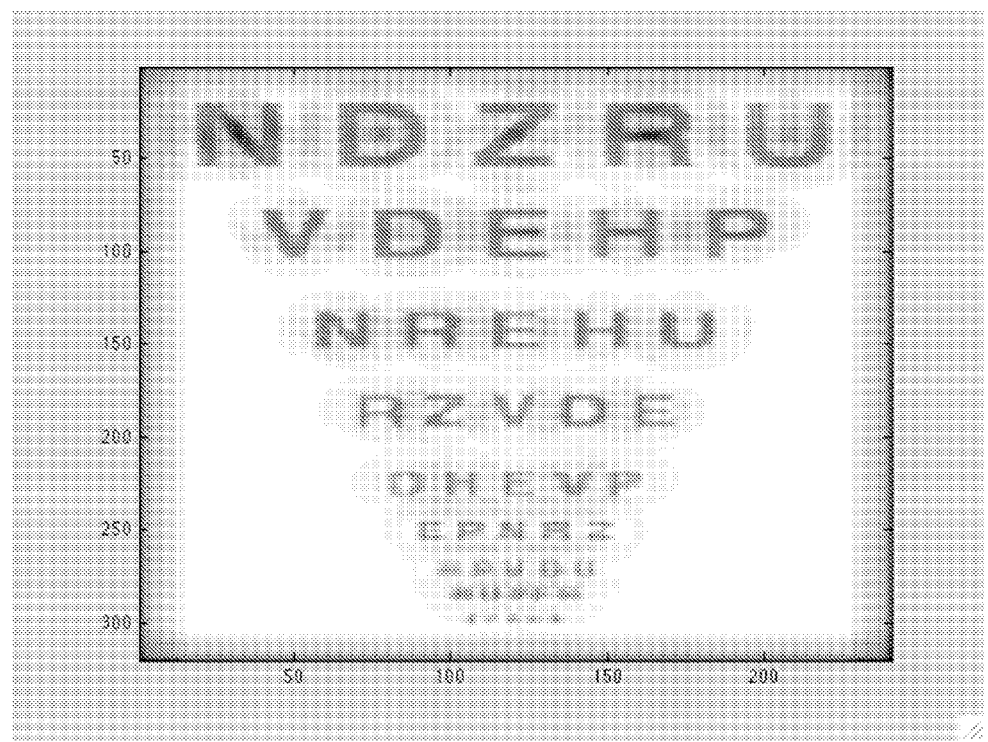
FIG. 5 illustrates the simulated retinal image of bifocal-corrected eye generated with opposite sign defocus and spherical aberration.

FIG. 4 illustrates simulated retinal image of bifocal eye generated with same sign defocus and spherical aberration. The defocused ghosts have been minimized and are almost invisible. FIG. 5 illustrates simulated retinal image of bifocal eye generated with opposite sign defocus and spherical aberration. Notice that the defocused ghosts are clearly visible. The visibility of the ghosts shown in FIG. 5 will be further increased as the CL, IOL or refractive surgery or implant is decentered relative to the pupil.

Certain exemplary embodiments, by controlling the SA in the distance and near optical zones will ensure that defocus and SA (or other similar radially symmetric asphericity) always have the same sign, and thus the ghost will be invisible (or at least significantly less visible) than would have been achieved with opposite sign defocus and SA. This is achieved by introducing sufficient negative SA into the distance correction, and ensuring that there is sufficient positive SA in the near correction. The respective negative and positive SA in the distance and near correction is achieved when on the eye, and thus can incorporate the eye's inherent SA into the design as needed. Levels of resulting positive and negative SA may vary from small (e.g. 0.1 microns) to large (e.g. 0.4 microns) across a 6 mm diameter pupil, but can be scaled to any pupil size and adjusted in level to achieve required visibility of ghost images. In some instances, SA may create radially symmetric changes in optical power across the lens or pupil. Examples of SA creating symmetric changes could be Seidel SA, Zernike SA, or any other gradual change in power as a function of the distance from the lens or pupil center. Such changes can be produced by shaping of the optical surface, manipulation of refractive index, and manipulation of the zone separations and profiles in diffractive bifocals. In one embodiment, sign of this SA is defined as positive if the power becomes more positive with distance from the center and negative if it the power becomes more negative with distance from the center.

Certain exemplary embodiments include a multifocal lens design including reduced or minimized ghosting. Some embodiments include a contact lens. Some embodiments include an IOL. Some embodiments include an ophthalmic surgical prescription rather than a separate corrective lens. Some embodiments include a refractive surgical correction, such as a LASIK correction. Some embodiments include monovision corrections and variants of this form of prescription often referred to as modified monovision.

Certain exemplary embodiments include a method of determining a multifocal prescription including reduced or minimized ghosting. Some embodiments include a spectacle lens. Some embodiments include a contact lens. Some embodiments include an IOL. Some embodiments include an ophthalmic surgical prescription rather than a separate corrective lens. Some embodiments include a LASIK prescription.

The embodiments of the invention illustrated and described in detail in the figures and foregoing description are illustrative and not limiting or restrictive. Only the presently preferred embodiments have been shown and described and all changes and modifications that come within the scope of the invention are to be protected. It should be understood that various features and aspects of the embodiments described above may not be necessary and embodiments lacking the same are also protected. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

This invention is distinct from all previous inventions that either increase SA or decrease SA by either introducing positive OR negative SA across the whole pupil or an individual optical zone. It requires specifically that the distance correction and near correction contain opposite sign SA to each other: negative SA in the distance correction and positive SA in the near correction.

While the invention has been described with reference to preferred and example embodiments, it will be understood by those skilled in the art that a variety of modifications, additions and deletions are within the scope of the invention, as defined by the following claims.

What is claimed is:

1. A multifocal diffractive ophthalmic lens, comprising:
   a base optic adapted to change the power of user's eye, the base optic having a distance optical correction portion and a diffractive element comprising a near optical correction portion,
      wherein the distance optical correction portion provides a distance correction power that includes a negative spherical aberration,
      wherein the near optical correction portion provides a near correction power that includes a positive spherical aberration of sufficient magnitude to remove ghost images that would otherwise be provided by the near optical correction when viewing a distance object, and
      wherein the distance optical correction portion provides a distance correction power that includes a negative spherical aberration of sufficient magnitude to remove ghost images that would otherwise be provided by the distance optical correction when viewing a near object,
      wherein the near optical correction portion produces only a positive spherical aberration, and wherein the distance optical correction portion produces only a negative spherical aberration.

2. The multifocal diffractive ophthalmic lens of claim 1, comprising an index of refraction generating a portion of the positive spherical aberration in the near power of the diffractive optic profile.

3. The multifocal diffractive ophthalmic lens of claim 1, wherein the base optic comprises a bifocal lens.

4. The multifocal diffractive ophthalmic lens of claim 1, wherein the base optic comprises a trifocal lens.

5. The multifocal diffractive ophthalmic lens of claim 1, wherein the base optic comprises a lens.

6. The multifocal diffractive ophthalmic lens of claim 1, wherein the base optic comprises a contact lens (CL).

7. The multifocal diffractive ophthalmic lens of claim 1, wherein the base optic comprises an intraocular lens (IOL).

8. The multifocal diffractive ophthalmic lens of claim 1, wherein the base optic comprises a corneal in-lay.

\* \* \* \* \*